US012599292B2

(12) United States Patent
Matthison-Hansen

(10) Patent No.: US 12,599,292 B2
(45) Date of Patent: Apr. 14, 2026

(54) ARTICULATED BENDING SECTION BODY FOR AN INSERTION ENDOSCOPE

(71) Applicant: AMBU A/S, Ballerup (DK)

(72) Inventor: Kaspar Mat Matthison-Hansen, Helsingør (DK)

(73) Assignee: AMBU A/S, Ballerup (DK)

( * ) Notice: Subject to any disclaimer, the term of this patent is extended or adjusted under 35 U.S.C. 154(b) by 417 days.

(21) Appl. No.: 17/921,573

(22) PCT Filed: Apr. 22, 2021

(86) PCT No.: PCT/DK2021/050122
§ 371 (c)(1),
(2) Date: Oct. 26, 2022

(87) PCT Pub. No.: WO2021/219178
PCT Pub. Date: Nov. 4, 2021

(65) Prior Publication Data
US 2023/0165443 A1 Jun. 1, 2023

(30) Foreign Application Priority Data

Apr. 27, 2020 (DK) ........................... PA 2020 70263

(51) Int. Cl.
*A61B 1/005* (2006.01)
*A61B 1/008* (2006.01)
(52) U.S. Cl.
CPC ............ *A61B 1/0057* (2013.01); *A61B 1/008* (2013.01)
(58) Field of Classification Search
CPC ..... A61B 1/0057; A61B 1/008; A61B 1/0055; A61B 1/00071; A61B 1/012; A61B 1/018
See application file for complete search history.

(56) References Cited

U.S. PATENT DOCUMENTS 4,796,607 A * 1/1989 Allred, III ........... A61B 1/0057
138/120
8,790,250 B2 7/2014 Petersen et al.
(Continued)

FOREIGN PATENT DOCUMENTS

JP 2942392 B2 * 8/1999 ............... A61B 1/00
JP 2009279254 A 12/2009
(Continued)

OTHER PUBLICATIONS

First technical report and search opinion in Danish Patent Application No. PA 2020 70263, Jul. 17, 2020, 9 pgs.
(Continued)

*Primary Examiner* — Anh Tuan T Nguyen
*Assistant Examiner* — Rynae E Boler
(74) *Attorney, Agent, or Firm* — Faegre Drinker Biddle & Reath LLP

(57) ABSTRACT

An endoscope with an articulated bending section body (1) including a number of segments (4) where at least one hinge member (5) is provided between any adjacent segment (4). Each segment (4) has a first surface (9, 9") and a second surface (10, 10') delimited by an outer rim. The first surface (9, 9") includes a first abutment part (11) adapted to abut the first opposing surface (10, 11) of an adjacent segment, wherein the first abutment part (11) is at a distance from the at least one hinge member (5) that is shorter than the shortest distance from the at least one hinge member (5) to the most remote part of the rim.

23 Claims, 6 Drawing Sheets

(56)                References Cited

U.S. PATENT DOCUMENTS

| | | | |
|---|---|---|---|
| 9,770,160 B2 | 9/2017 | Okaniwa et al. | |
| 9,968,241 B2 | 5/2018 | Luel | |
| 10,165,931 B2 | 1/2019 | Petersen et al. | |
| 10,321,804 B2 | 6/2019 | Jacobsen et al. | |
| 11,357,392 B2 | 6/2022 | Matthison-Hansen et al. | |
| 11,471,031 B2 | 10/2022 | Jensen | |
| 2005/0222499 A1* | 10/2005 | Banik | A61B 1/0676 |
| | | | 600/156 |
| 2006/0199999 A1* | 9/2006 | Ikeda | A61B 34/71 |
| | | | 600/141 |
| 2009/0209819 A1* | 8/2009 | Kitagawa | A61B 1/0055 |
| | | | 600/142 |
| 2009/0234186 A1 | 9/2009 | Lin et al. | |
| 2010/0168519 A1* | 7/2010 | Matsuo | A61B 1/00078 |
| | | | 600/139 |
| 2011/0306831 A1 | 12/2011 | Køhnke et al. | |
| 2012/0170970 A1* | 7/2012 | Kitagawa | A61B 1/0011 |
| | | | 403/81 |
| 2014/0243592 A1 | 8/2014 | Kato et al. | |
| 2016/0227985 A1 | 8/2016 | Ikeda et al. | |
| 2018/0310804 A1 | 11/2018 | Tanaka et al. | |
| 2020/0100648 A1 | 4/2020 | Jensen | |
| 2020/0113412 A1 | 4/2020 | Jensen | |
| 2020/0113415 A1 | 4/2020 | Kristensen | |
| 2020/0196835 A1 | 6/2020 | Qvist et al. | |
| 2020/0222666 A1 | 7/2020 | Chan et al. | |
| 2021/0321857 A1* | 10/2021 | Nelson | A61B 1/00135 |

FOREIGN PATENT DOCUMENTS

| | | | | |
|---|---|---|---|---|
| WO | WO-2008047797 A1 * | 4/2008 | | A61B 1/0055 |
| WO | 2014106511 A1 | 7/2014 | | |
| WO | 2019018736 A2 | 1/2019 | | |

OTHER PUBLICATIONS

International Search Report and Written Opinion for International Application No. PCT/DK2021/050122, Aug. 12, 2021, 11 pgs.
Examination Report issued in European Application No. 21725694.0, dated May 28, 2025, 5 pages.

* cited by examiner

ARTICULATED BENDING SECTION BODY FOR AN INSERTION ENDOSCOPE

CROSS REFERENCE TO RELATED APPLICATIONS

This application is a National Stage entry under 35 U.S.C. § 371 of International Application No. PCT/DK2021/050122, filed Apr. 22, 2021, which claims priority from and the benefit of Danish Patent Application No. PA 2020 70263, filed Apr. 27, 2020; said applications are incorporated by reference herein in their entirety.

TECHNICAL FIELD

The present disclosure related to insertion endoscopes in particular to the articulated bending section of such an endoscope.

BACKGROUND

Insertion endoscopes typically comprises a handle at the proximal end gripped by an operator and a flexible elongated insertion tube terminated at the distal end in a tip part at the end of a highly bendable, e.g. articulated, bending section, controllable by the operator. The tip part normally comprises a visual inspection means such as a camera, and illumination means such as LED's or exit apertures of light fibres and whatever optics is needed in that connection. Electrical wiring for the camera and other electronics such as the LED lighting run along the inside of the elongated insertion tube from the handle to the tip at the distal end. When, as mentioned, the illumination is instead fibre-optic, the optical fibres run along inside of the elongated insertion tube.

Thus, the controllable bending section is normally an articulated section at the distal tip of the elongated insertion tube that can be controlled by the operator via control knobs arranged on the handle. Typically, this control is effected by tensioning or slacking pull wires also running along the inside of the elongated insertion tube from the articulated tip part to a control mechanism of the handle. Furthermore, a working channel may run along the inside of the elongated insertion tube from the handle to the tip, e.g. allowing liquid to be removed from the body cavity or allowing the insertion of surgical instruments or the like into the body cavity.

Thus, using the controls allows the operator to advance the distal tip of the endoscope to a desired location by means of a series of actions involving inter alia bending the bending section in a desired direction, advancing the elongated insertion tube and turning the elongated insertion tube by turning the handle which is rigidly connected thereto. Navigating a tortuous path of bends and turns to a location of interest may subject the elongated insertion tube including the distal controllable bending section to substantial forces including compression, torsion, and bending. The main body of the elongated insertion tube is essentially only bendable enough to follow the direction taken by the articulated bending section. In fact, it could be said that it is an essential part of the purpose of the elongated insertion tube to transmit the longitudinal pushing forces and rotary torsional forces from the handle to the distal end of the elongated insertion tube in order to allow these maneuvers.

It is well known to provide the articulated bending section using a moulded single-piece bending section body comprising a distal tip-part segment for accommodating the camera etc. as explained initially, a proximal connection segment for connection to the elongated insertion tube body, and a number of more or less identical articulated intermediate segments. An example of such a moulded single-piece bending section body is found in WO2014/106511, incorporated herein by reference.

Although the moulded single-piece bending section body of WO2014/106511 has shown quite successful there are some drawbacks when used for bending sections designed for very large bending angles.

One such drawback relates to the external sheath which, as explained in WO2014/106511, normally covers the bending section. This sheath is formed of a highly elastic and very thin polymer material, typically in the range of 70 μm to 100 μm, so as to not inhibit the bending properties of the articulated bending section.

When bending the bending section there will on the concave side i.e. where the narrower radius is be a tendency for the elastic sheath to fold into the gaps between neighboring articulated segments and get caught, i.e. pinched between the outer parts of the peripheries of the adjacent segments. Though this is not in itself a problem it may lead to problems. The pinching forces themselves are normally insufficient to penetrate or puncture the sheath and thereby damage the integrity and protective sealing properties of the sheath. However, the pinching has a secondary effect in that holding the sheath firmly in a vise like manner will make the fold enter deeply into the gap between adjacent segments where it may contact the pull-wires and be subject to abrasion during repeated bending motions, which may in the end damage the integrity of the sheath.

BRIEF DESCRIPTION OF THE DISCLOSURE

It is the object of the present disclosure to overcome this drawback.

According to a first aspect of the present disclosure this drawback is overcome by providing an endoscope comprising an articulated bending section body, said body comprising number of segments including a proximal end segment, a distal end segment and a number of intermediate segments arranged between the proximal segment and the distal segment, where at least one hinge member is provided between the proximal end segment and one of said intermediate segments, where at least one hinge member is provided between the distal end segment and one of said intermediate segments, and where at least one hinge member is provided between any adjacent intermediate segments; where each intermediate segment has a first surface and a second surface, each of said surfaces being delimited by an outer rim, where said first surface faces a first opposing surface of a first adjacent segment, and said second surface faces a second opposing surface of a second adjacent segment, where said first surface comprises a first abutment part adapted to abut the first opposing surface of said adjacent segment, and said second surface comprises a second abutment part adapted to abut said second opposing surface of said second adjacent segment, wherein said first abutment part is at a distance from said at least one hinge member that is shorter than the shortest distance from the at least one hinge member to the most remote point on the rim.

By providing an abutment part in this manner the outermost parts of the rim as seen from the hinge members are prevented from firmly pinching and holding the outer sheath. Rather any fold that the outer sheath may form inwardly at bending will be accommodated and held loosely in the gap formed. Consequently, any part of the fold of the sheath that may get into contact with the pull-wires will be able to frictionally follow movements of the pull-wires thereby avoiding abrasive interaction between the pull-wires and the sheath.

According to a second aspect of the invention the object is achieved by system comprising an endoscope according to the first aspect of the invention and a display unit connectable to said endoscope According to a preferred embodiment of the present disclosure, said at least one segment comprises a through pull-wire passage between said first surface and said second surface so as present a pull-wire opening in each of said first and second surfaces, and wherein said pull-wire opening in said first surface is located in said abutment part. By this arrangement of the pull-wire openings the risk that the sheath even gets into engagement with the pull-wires is further mitigated. A sheath pocket is formed by the portions of the first surface and the second surface radially distal of where the abutment parts abut, such that when the outer sheath is in the sheath pocket it does not extend radially inward of where the abutment parts abut.

According to a further preferred embodiment, said abutment part comprises, in a relaxed as manufactured state of said articulated bending section, a plane surface, a pull-wire opening being located in said plane surface.

According to yet a further preferred embodiment, said abutment part comprises a rounded edge, said rounded edge being located at a distance from said at least one hinge member that is longer than the longest distance from the at least one hinge member to the most remote part of a pull-wire opening. This further inhibit any tendency of the inward fold of the outer sheath to get caught and pinched between adjacent segments.

According to an alternative preferred embodiment, said abutment part comprises a rounded edge, said rounded edge being at least partially intersected by a pull-wire opening. This allows the pull-wires to be provided as far as possible from the hinges for maximum bending torque yet still protects the folds of the outer sheath against abrasion.

According to yet another preferred embodiment, both said first surface and said opposing surface of the adjacent segment comprise abutment parts. This further increases the size of the gap for accommodating folds of the outer sheath, as compared to the abutment part abutting directly against a plane opposed surface.

According to a preferred embodiment a pull-wire passage continues through the hinge members from one intermediate segment to the next. In this way a continuous path for guiding the pull-wire may be provided.

BRIEF DESCRIPTION OF THE FIGURES

The disclosure will now be made in greater detail based on non-limiting exemplary embodiments and the appended drawings on which.

DETAILED DESCRIPTION

Figure 11:
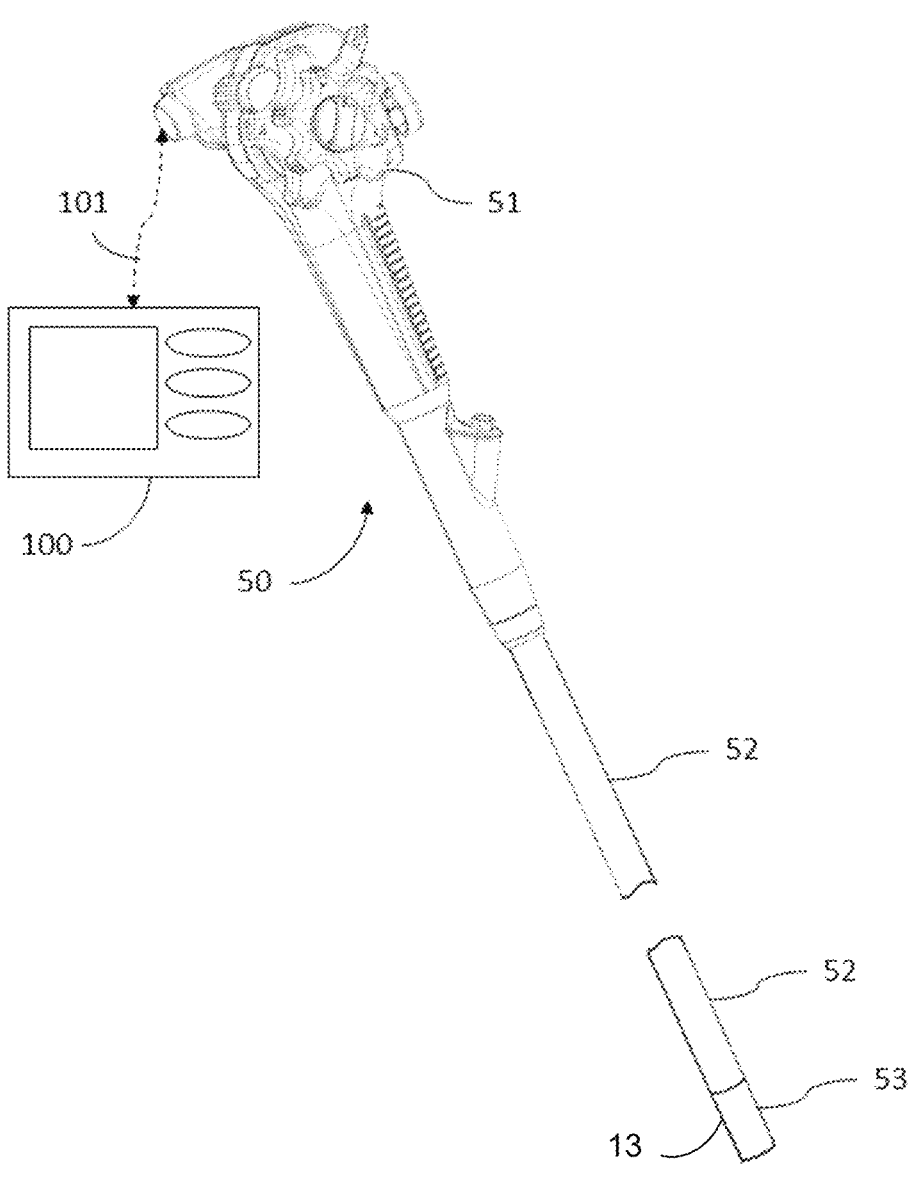
FIG. 11 shows a system comprising an endoscope according to the present disclosure and a display device.

Turning first to FIG. 11 a system comprising a display device 100 and an endoscope 50 connectable to the display device 100 by means of a cable 101 or a wireless connection is shown. The endoscope 50 comprises a handle 51 at the proximal end and an insertion tube 52 connected to a bending section 53 forming part of the distal end of the endoscope 50. The bending section 53 comprises an articulated bending section body 1. The bending section body 1 is not visible in FIG. 11 because it is covered by a thin external sheath 13. Reference is therefore now made to FIGS. 1 to 10.

Figure 1:
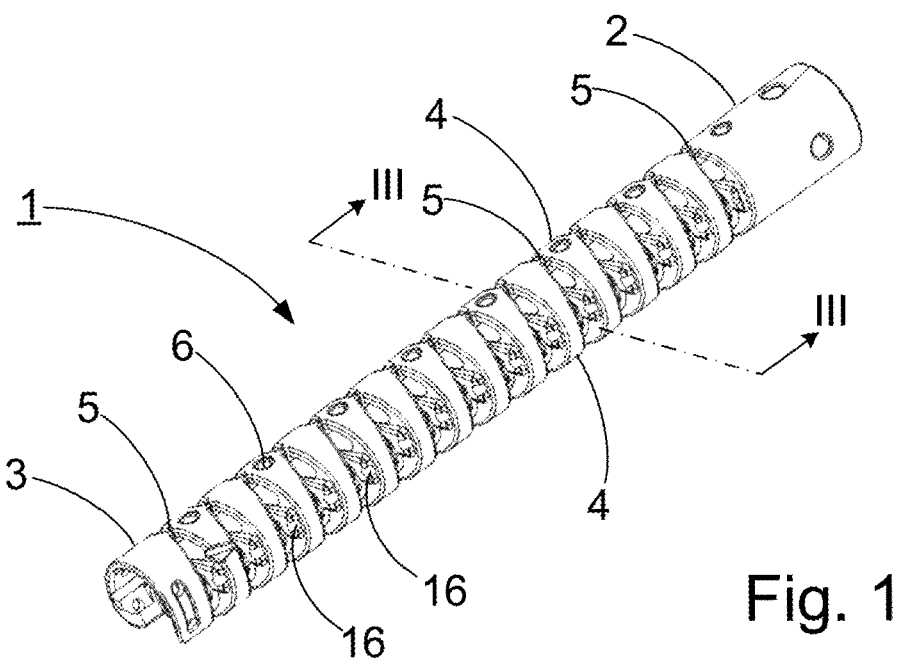
FIG. 1 shows an isometric view of a first embodiment of a bending section body according to the present disclosure in a relaxed, as made, condition.

In FIG. 1 an articulated bending section body 1 according to a first embodiment of the disclosure is shown. The articulated bending section body comprises 1 a proximal end segment 2 at one end adapted to be connected to an insertion tube body (not show). At the other end the articulated bending section body 1 comprises a distal end segment 3 for at least partly accommodating illumination devices, an electronic vision device, such as a camera, and other electronics. Between the proximal end segment 2 and the distal end segment 3 a number of intermediate segments 4 are located. Each of the intermediate segments 4 is connected to a neighboring segment, be it to another intermediate segment 4 to the proximal end segment 2 or the distal end segment 3 by means of hinge members 5, such as foil hinges. The intermediate segments 4 are preferably more or less identical, except for inlets 6, ejector marks etc. from manufacture. In some cases, as will be discussed below, some of the intermediate segment 4 may be mirror images of other intermediate segments 4 but otherwise identical. Accordingly, as can best be seen in FIG. 2, the hinge members 5 of the first embodiment all lie in the same plane S-S. The outer surface 7 of each hinge member 5 is preferably circular so as to define a cylindrical mantle surface delimited by a rim 8 and give the bending section body 1 an overall cylindrical shape in the relaxed, as made, state. That is to say as manufactured and without any external bending forces acting upon it. The plane S-S in which the hinge members 4 lie thus defines a longitudinal mirror symmetry plane of the bending section body 1.

The outer rim 8 defines a transition between the outer surface 7 and respective opposing surfaces 9, 10 of adjacent segments 4. Since the segments 4 are essentially identical, primes will be used in the following to distinguish one segment 4 from the adjacent neighboring segments 4' and 4", although the features described are equally applicable to them. That is to say, the intermediate segment 4 shown in FIG. 2 comprises a first surface 9 and a second surface 10, where the first surface 9 faces an opposing surface 10', of an adjacent segment 4' and the second surface 10 faces an opposing surface 9" of an adjacent segment 4".

Raised above the opposing surfaces 9, 10 are a number of abutment parts 11, 11', 11". When the bending section bends opposing pairs of abutment parts 11, 11'; 11, 11" will abut and prevent the bending section from bending any further. The abutment as such is common to all embodiments, and will, as can be seen from FIG. 4, provide a spacing between the outermost edges 12, 12'; 12, 12" of adjacent outer rims 8 of neighboring segments 4 thereby forming a gap 14 preventing pinching of the outer sheath 13, a sheath pocket 14' being formed between the outer rims 8 (through the gap 14), the distal abutment portion 11 and the proximal abutment portion 11' when the distal abutment portion and the proximal abutment portion abut each other. As seen in FIG. 4, the outer sheath 13 folds smoothly into the sheath pockets 14' without extending to the abutment. The abutment however may differ. As will be understood from the geometry of the embodiment of FIGS. 1 to 3, only the outermost edges 15, 15' of the abutment portions 11, 11' abut, whereas in the embodiment of FIG. 4 the abutment parts have inclined surfaces allowing a larger surface area of the opposing abutment parts 11, 11' to abut. Please note that apart from the primes the same reference numerals are used for corresponding items in different embodiments throughout this description.

Figure 2:
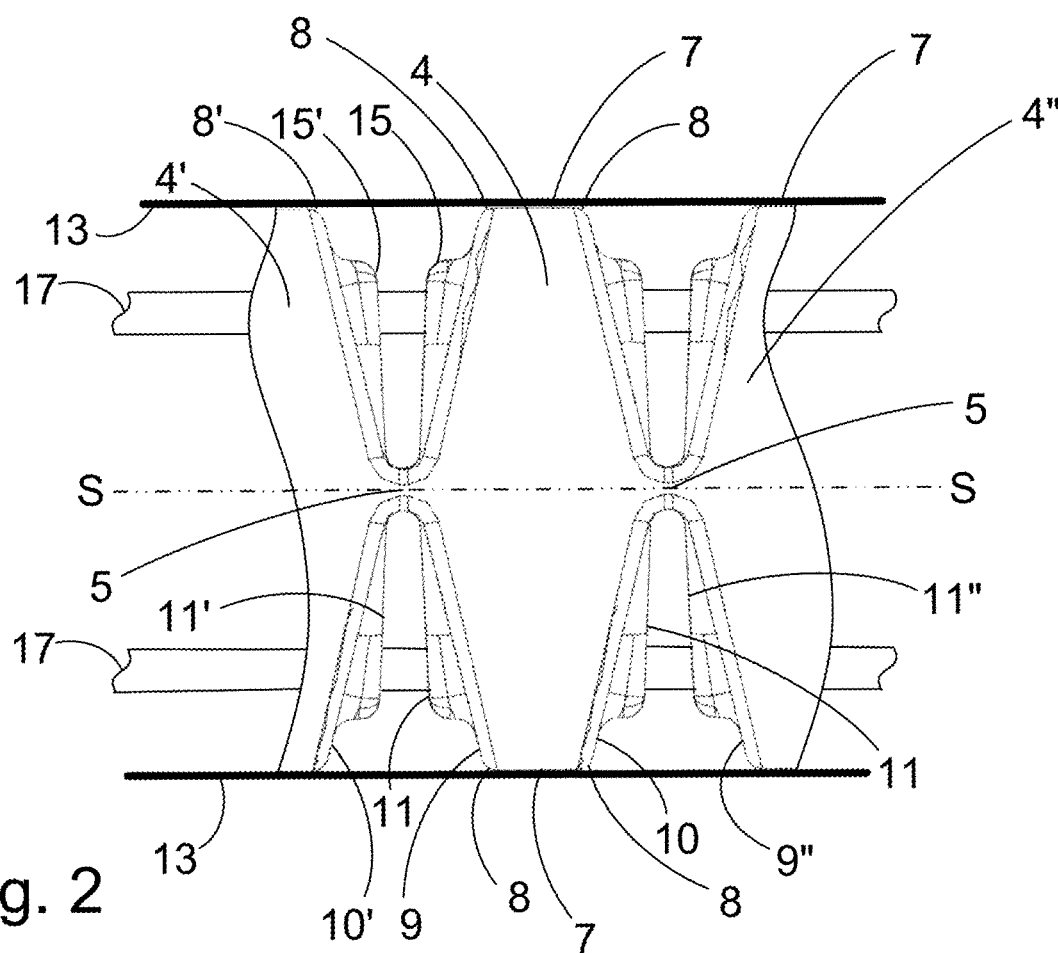
FIG. 2 shows a partial top view of an intermediate segment and two adjacent segments of the first embodiment of FIG. 1.

As can be seen, in the embodiment in FIG. 2, the pull-wire openings 16 of the through pull-wire passages are at least partially but preferably in full located closer to the hinge members 5 than the outermost edges of the abutment parts of adjacent segments 4, 4', i.e. located between the hinge members and the outermost edges of the abutment parts. Thus, when the outermost edges 15, 15' of the abutment parts abut, the gap 14 will remain open so that the outer sheath 13 is not pinched by the outer rims 12 and the sheath pocket 14' will be inwardly closed and further prevent the pull-wires 17 from engaging the fold of the outer sheath 13. Although the present explanation makes reference to plural pull-wires, the skilled person will understand that features relating to pull-wires may all be applicable to a single pull-wire and not only several, such as typically two or four.

Figure 4:
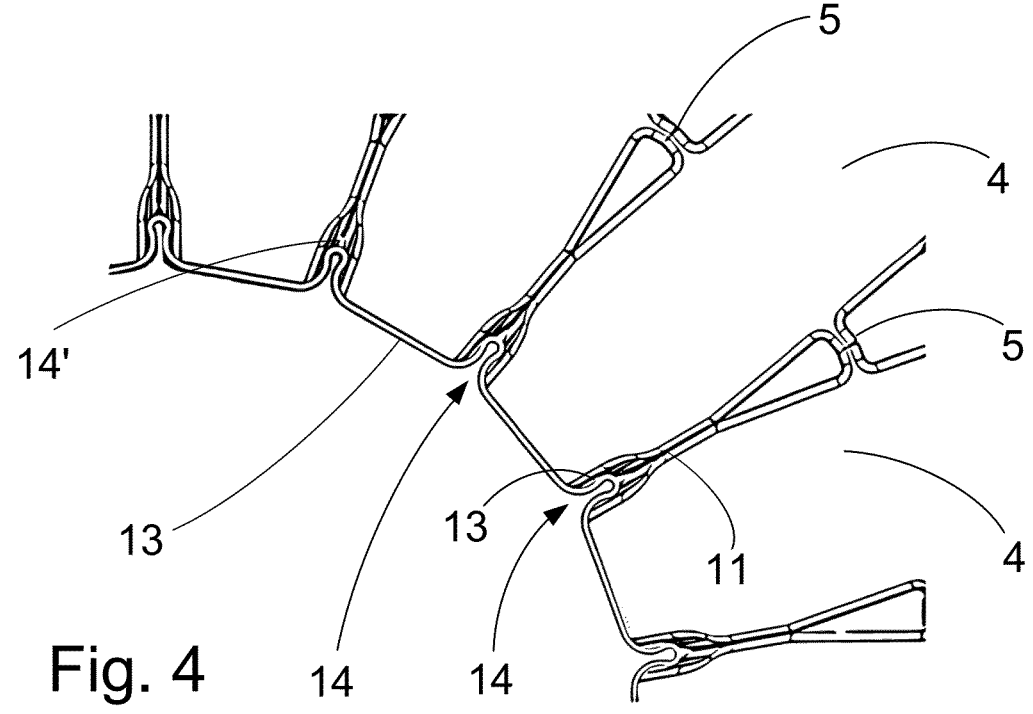
Figure 5:
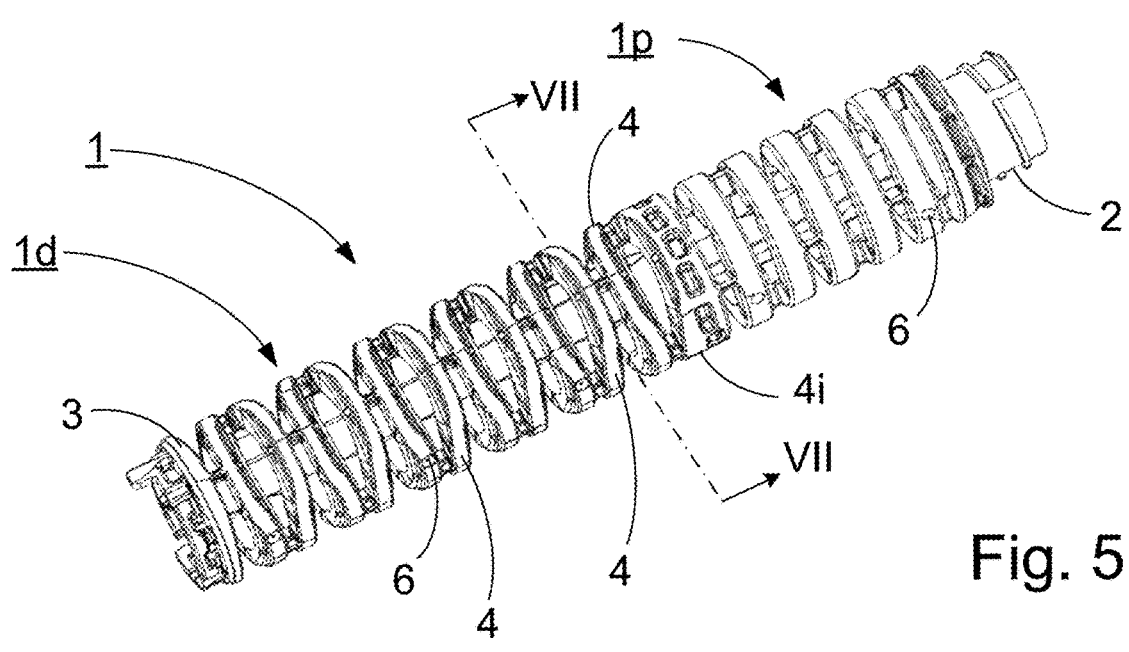
FIG. 5 shows an isometric view of a second embodiment of a bending section body according to the present disclosure in a relaxed, as made, condition.
Figure 6:
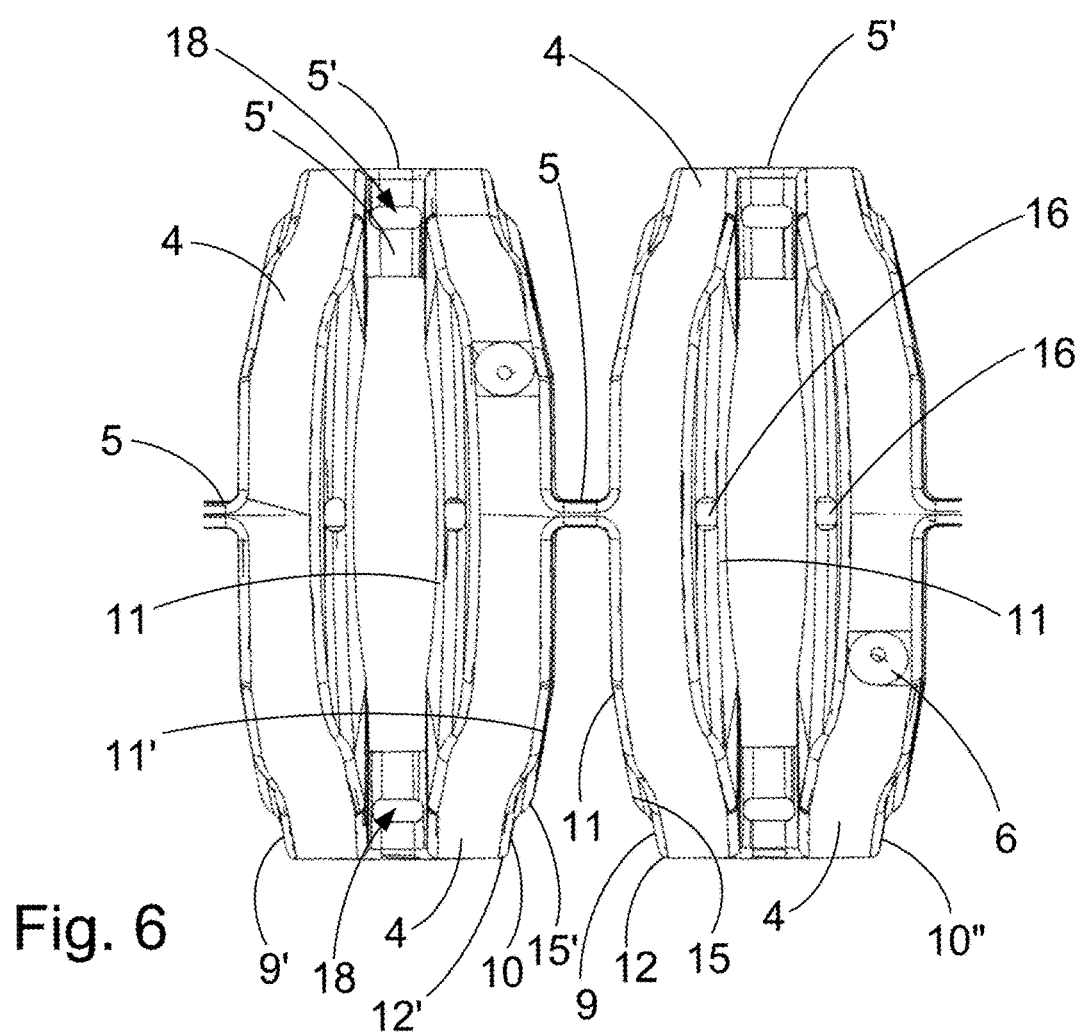
FIG. 6 shows a partial top view of four intermediate segments of the first embodiment of FIG. 5.
Figures 7, 8:
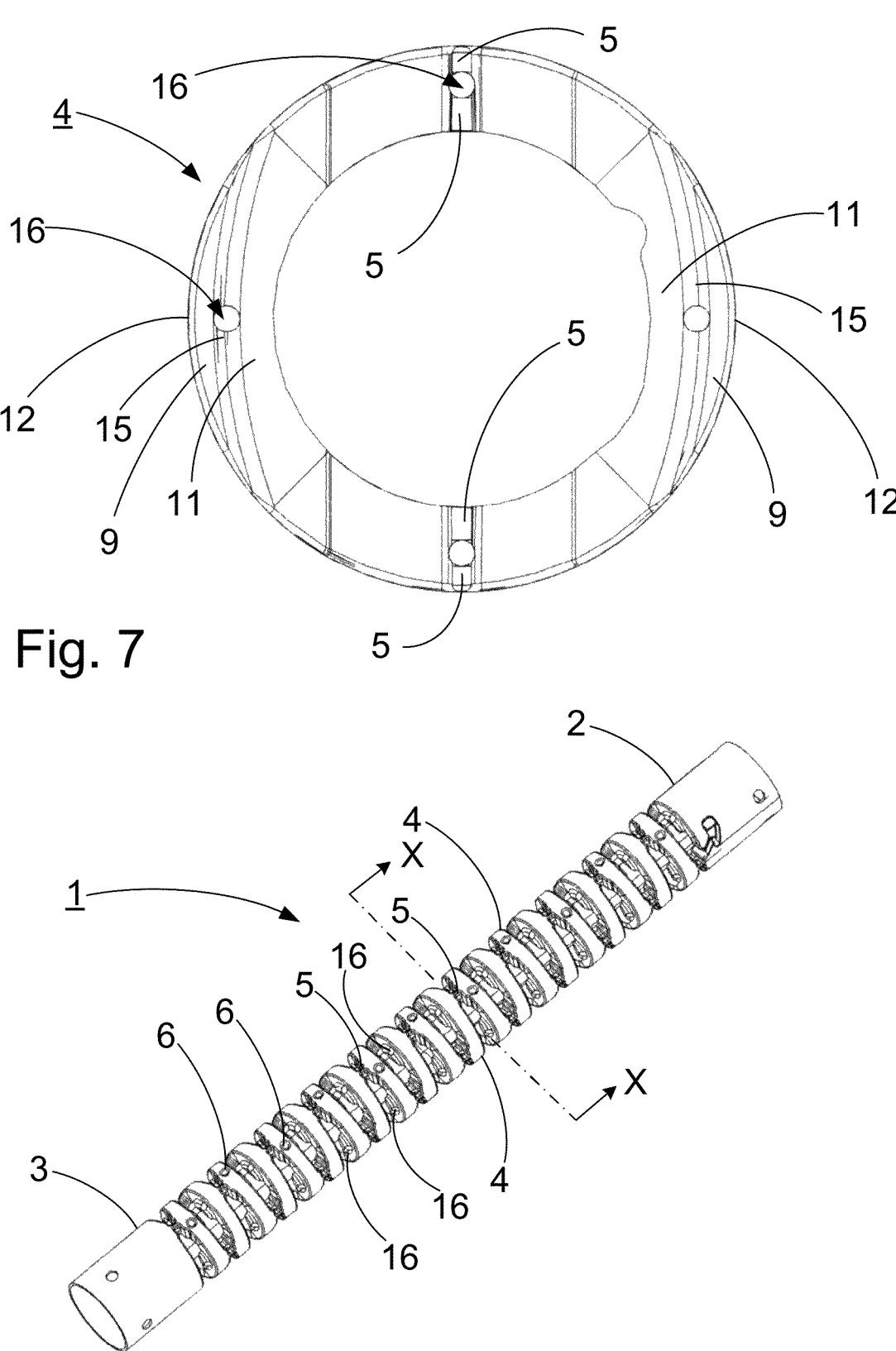
FIG. 7 shows a cross-sectional view of the second embodiment taken along the line VII-VII in FIG. 5.
FIG. 8 shows an isometric view of a third embodiment of a bending section body according to the present disclosure in a relaxed, as made, condition.

Turning now to FIGS. 5 to 7 a different embodiment of a bending section body 1 according to the disclosure is shown. The bending section body 1 in this embodiment differs from the embodiments of FIGS. 1 to 4, which may bend in one plane only, in that it may bend in two planes. It furthermore differs in that it comprises an active bending section 1*d* on the distal side of an interface segment 4*i* in FIG. 5 and a passive bending section 1*p* on the proximal side of the interface segment 4*i*. In the passive bending section 1*p* the pull-wires 1 are guided in sheaths according to the Bowden principle, the sheaths being terminated in the interface segment 4*i* with only the pull-wires 17 extending into the active bending section 1*d*.

As can be seen from FIG. 6 the intermediate segments 4 of the active bending section are arranged in mirror image pairs of otherwise identical intermediate segments. That is to say all of the intermediate segments 4 illustrated in FIG. 6 are identical if looked at individually but have a high degree rotational symmetry so that by a rotation of 90 degrees each intermediate segment will look like its own mirror image, except for details not relevant for the disclosure such as e.g. moulding inlets 6 and the like. Like in the previous embodiments, the opposing pairs of first and second surfaces 9, 10 have a number of abutment parts 11. When the bending section bends opposing pairs of abutment parts 11, 11' will abut and prevent the bending section from bending any further. Because of the overall symmetry this applies equally to both of the bending planes i.e. bending plane in which the hinges members 5 lie as well as the bending plane in which the hinges members 5' lie. As can further be seen in FIG. 6 there are essentially four hinge members 5, 5' between each pair of intermediate segments 4, because each of the hinge members symmetrically arranged at either side is de facto split in two by a gap 18 coinciding with the pull-wire openings 16, so as to allow the pull-wires 17 (not shown in FIG. 6) to pass between two intermediate segments 4, in other words the pull-wire passages continue through the hinge members from one intermediate segment to the next.

Turning to the end view of an intermediate segment 4 in FIG. 7 the details of the abutment parts 11 raised above the surface 9 can be seen. Comparison with FIG. 2 will reveal that the outermost edge 15 of the abutment part reaches all the way to the outer rim 12 at a location closer to the hinges, whereas in the embodiment of FIG. 2 it is located more centrally on the surface 9. Moreover, whereas the outermost edge is generally straight in the embodiment of FIG. 2 it describes a curve in the embodiment of FIG. 7. The curve is preferably a circle sector of a large radius than the radius of the overall intermediate segment 4. The pull-wire openings coincide more or less with the rounded outermost edge 15 of the abutment part 11. This still prevents the outer sheath 13 to get into contact with the abrasive pull-wire 17 when the bending section body 1 bends under the tension of the pull-wire 17.

Figures 9, 10:
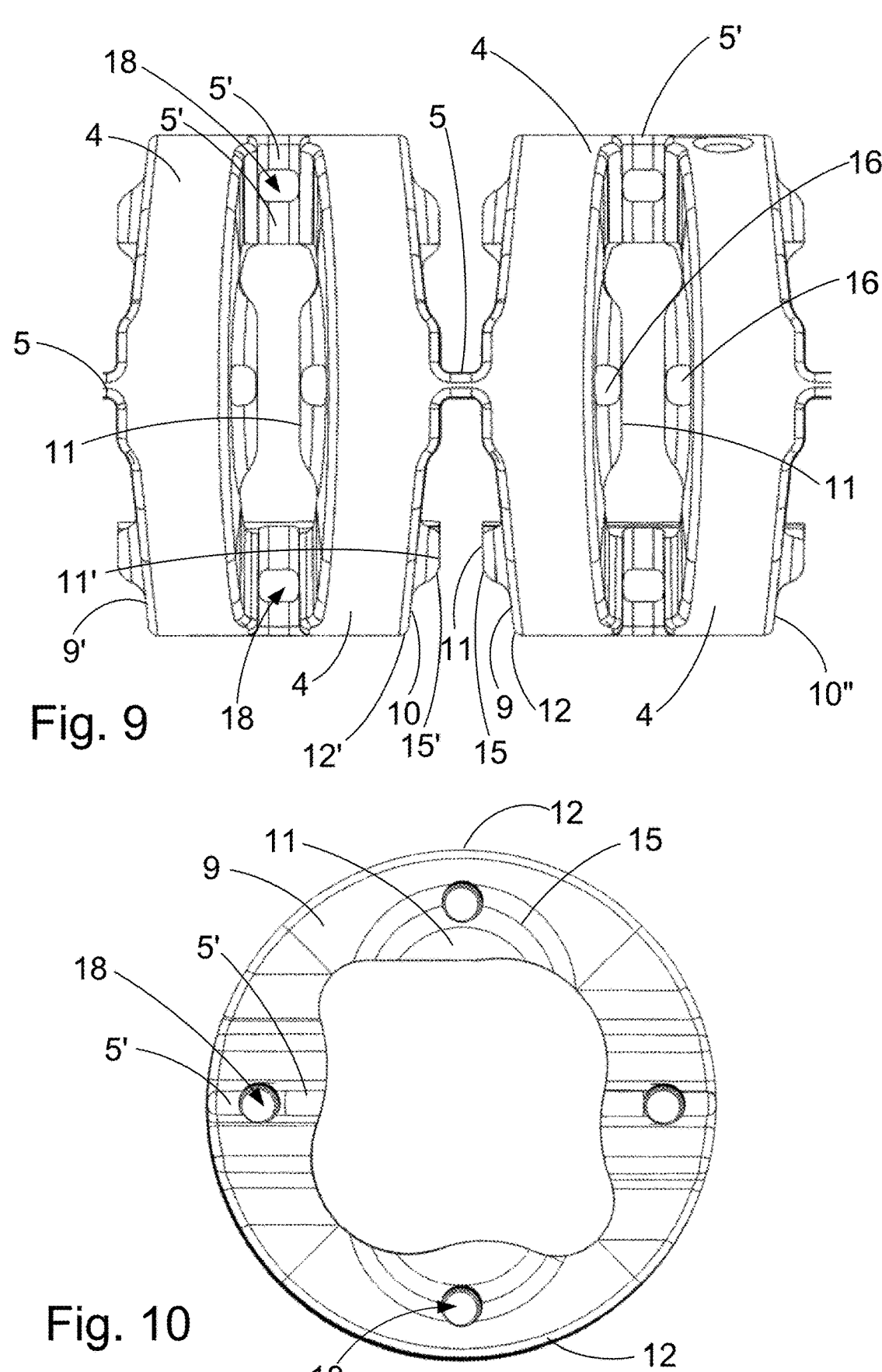
FIG. 9 shows a partial top view of four intermediate segments of the third embodiment of FIG. 8.
FIG. 10 shows a cross-sectional view of the first embodiment taken along the line X-X in FIG. 8.

Similarly, to the embodiment of the bending section body of FIGS. 5 to 7, the bending section body 1 of FIGS. 8 to 10 is devised to bend in two planes. It lacks, however, the division in a passive and an active bending section part. Accordingly, it consists entirely of identical intermediate segments 4 between the proximal end segment 2 and the distal end segment 3. Also in this embodiment the rotational symmetry is such that turning an intermediate segment 4 by 90 degrees makes it correspond to its own mirror image. To allow bending in two planes defined by hinges 5, 5' bending section body 1 comprises pairs of intermediate segments 4 that are mirror images of each other, as is also the case in the embodiment of FIGS. 5 to 7.

Please note that as compared to FIGS. 5 to 7 the outer sheath 13 and the pull-wires 17 have been omitted in FIGS. 8 to 10 for illustration purposes, but would essentially correspond to FIGS. 5 to 7. Accordingly, when tensioning a pull-wire 17 the bending section body 1 will bend, the bending direction depending on which of the four pull-wires 17 are tensioned. When bending, opposing abutment parts 11, 11' will abut at the outer edges 15, 15 thereby blocking the outer rims 12, 12' of the intermediate segments from fully approaching each other, so that the gap 14 is formed. As in the other embodiments the sheath pocket 14' will accommodate a fold of the outer sheath 13 in a manner preventing it from being pinched by the outer rims. Instead, it will be held as a loose fold that may follow movements of the pull-wire 17, preferably with geometrical bond, i.e. follow without rubbing, so as to avoid any abrasion that could ruin the outer sheath 13. Preferably, the outer edge 15 in this and the other embodiments disclose is also rounded so as to not provide any sharp edges that might still pinch the fold in the outer sheath 13. Preferably, the outer edge 15 in this and the other embodiments disclose is also rounded so as to not provide any sharp edges that might still pinch the fold in the outer sheath 13.

As will be clear from FIG. 10 the outer edge 15 of the abutment part describes a curve, preferably, a circle sector, albeit with a narrower radius that the overall radius of the intermediate segments 4. Apart from having a curvature, the outer edge 15 is preferably also rounded to further prevent pinching of the outer sheath 13. In this and other embodiments it has been found that if the pull-wire opening 16 intersects with the rounded outer edge 15 it suffices to protect the outer sheath 13 from abrasion it need not be located in a fully retracted position away from the rounded edge and closer to the plane of the hinge members.

Figure 3:
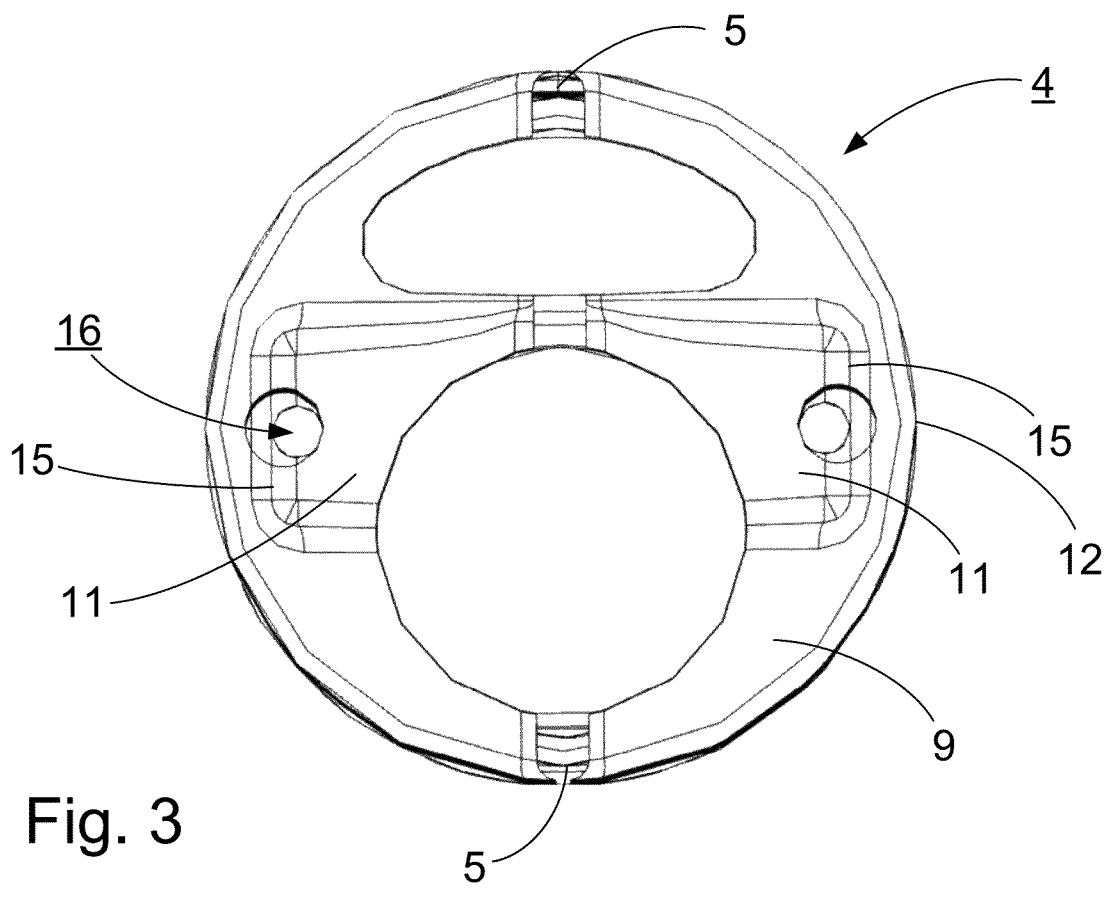
FIG. 3 shows a cross-sectional view of the first embodiment taken along the line III-III in FIG. 1, FIG. 4 schematically shows a part of a bending section body according to the disclosure in a maximally bent state.

As can be seen by comparison between e.g. FIGS. 3, 7 and 10. The outer edge 15 is in all embodiments closer to the plane defined by the hinges 5, than the distance from the hinges to the most remote part of the outer rim 12 as seen from the hinges, i.e. the most remote point on the outer rim 12 as seen from the hinges, so as to allow the outer edges 15 to abut and form the gap 14 between the remote parts outer rims 12 that could otherwise pinch the outer sheath 13.

Although all shown embodiments have mirror image symmetry, with raised abutment parts 11 butting corresponding or identical abutment parts 11 on adjacent segments, such as another intermediate segment 4, a proximal end segment 2, a distal end segment 3 or even an interface segment 4i this is not a prerequisite for the functionality of the bending section body. A raised abutment part on one intermediate segment could also just abut directly on a plane opposing surface 9, 10 and still form a sufficient gap 14 by blocking the outer rims 12, 12' of adjacent segments.

What is claimed is:

1. An endoscope comprising:

an articulated bending section body including segments interconnected by hinge members on a first bending plane, the segments including a proximal segment, a distal segment and intermediate segments arranged between the proximal segment and the distal segment, a sheath positioned over the articulated bending section body; and a pull-wire, wherein each intermediate segment comprises a pull-wire passage, an outer rim, a distal surface and a proximal surface, the distal surface of one intermediate segment facing the proximal surface of another segment positioned adjacent to the one segment, the proximal surface and the distal surface each extending from the outer rim of the respective intermediate segment to a hinge member of the hinge members, the pull-wire extending through the pull-wire passages, wherein the one intermediate segment comprises a distal abutment portion and the another intermediate segment comprises a proximal abutment portion, wherein the pull-wire is configured to cause the distal abutment portion of the one intermediate segment and the proximal abutment portion of the another intermediate segment to abut each other at a location intermediate the outer rims and the hinge member to maintain apart the outer rim of the one intermediate segment from the outer rim of the another intermediate segment, a sheath pocket being formed between the outer rims, the distal abutment portion and the proximal abutment portion when the distal abutment portion and the proximal abutment portion abut each other, wherein each of the pull-wire passages comprises a radially outward peripheral portion and a radially inward peripheral portion radially opposite the radially outward peripheral portion, the radially outward peripheral portion limiting radially outward movement of the pull-wire, wherein the radially outward peripheral portion of the pull-wire passage is radially inward of the sheath pocket to prevent contact between the pull-wire and the sheath, wherein the distal abutment portion of the one intermediate segment and the proximal abutment portion of the another intermediate segment abut each other when the articulated bending section body is bent at a maximum angle of the first bending plane, and wherein when the articulated bending section body is bent at the maximum angle of the first bending plane a gap is formed between the outer rim of the one intermediate segment and the outer rim of the another intermediate segment, and wherein the sheath extends through the gap and into the sheath pocket no further than the location where the distal abutment portion of the one intermediate segment and the proximal abutment portion of the another intermediate segment abut.

2. The endoscope of claim 1, wherein the distal abutment portion extends distally across a plane passing through the outer rim of the respective intermediate segment and the hinge member.

3. The endoscope of claim 1, wherein the sheath extends into the sheath pocket without contacting the pull-wire.

4. The endoscope of claim 1, wherein the segments interconnected by the hinge members on the first bending plane comprise a passive section of the articulated bending section body, the articulated bending section body further comprising an active section, the intermediate segments of the active section being interconnected by hinge members on the first bending plane and on a second bending plane.

5. The endoscope of claim 4, wherein the pull-wire passages of the intermediate segments in the active section extend through a hinge member of the hinge members on the second bending plane.

6. The endoscope of claim 4, wherein the intermediate segments in the active section comprise pairs of intermediate segments, each pair connected to another pair by the hinge members on the first bending plane, and each intermediate segment of the pair connected to the other by the hinge members on the second bending plane.

7. The endoscope of claim 1, wherein each intermediate segment comprises a pull-wire passage extending between a pull-wire opening in the distal surface and a pull-wire opening in the proximal surface, and wherein the pull-wire opening in the distal surface is located in the abutment portion.

8. The endoscope of claim 1, wherein in each of the intermediate segments the pull-wire passage extends between a pull-wire opening in the distal surface and a pull-wire opening in the proximal surface, and the distal abutment portion comprises a rounded edge located radially outwardly from the pull-wire opening in the distal surface.

9. The endoscope of claim 1, wherein in each of the intermediate segments, the pull-wire passage extends between a pull-wire opening in the distal surface and a pull-wire opening in the proximal surface, the distal abutment portion comprises a rounded edge, and the rounded edge is at least partially intersected by the pull-wire opening in the distal surface.

10. The endoscope of claim 1, wherein the distal abutment portion and the proximal abutment portion comprise plane surfaces.

11. The endoscope of claim 10, wherein the articulated bending section body is bent at a maximum angle when the plane surfaces abut each other.

12. The endoscope of claim 10, wherein the pull-wire opening in the distal surface and the pull-wire opening in the proximal surface are located in the plane surfaces.

13. A system comprising:

an endoscope; and a display unit connectable to said endoscope, wherein the endoscope comprises:

an articulated bending section body including segments interconnected by hinge members on a first bending plane, the segments including a proximal segment, a distal segment and intermediate segments arranged between the proximal segment and the distal segment, a sheath positioned over the articulated bending section body; and a pull-wire, wherein each intermediate segment comprises a pull-wire passage, an outer rim, a distal surface and a proximal surface, the distal surface of one intermediate segment facing the proximal surface of another segment positioned adjacent to the one segment, the proximal surface and the distal surface each extending from the outer rim of the respective intermediate segment to a hinge member of the hinge members, the pull-wire extending through the pull-wire passages, wherein the one intermediate segment comprises a distal abutment portion and the another intermediate segment comprises a proximal abutment portion, wherein the pull-wire is configured to cause the distal abutment portion of the one intermediate segment and the proximal abutment portion of the another intermediate segment to abut each other at a location intermediate the outer rims and the hinge member to maintain apart the outer rim of the one intermediate segment from the outer rim of the another intermediate segment, a sheath pocket being formed between the outer rims, the distal abutment portion and the proximal abutment portion when the distal abutment portion and the proximal abutment portion abut each other, wherein each of the pull-wire passages comprises a radially outward peripheral portion and a radially inward peripheral portion radially opposite the radially outward peripheral portion, the radially outward peripheral portion limiting radially outward movement of the pull-wire, wherein the radially outward peripheral portion of the pull-wire passage is radially inward of the sheath pocket to prevent contact between the pull-wire and the sheath, wherein when the distal abutment portion of the one intermediate segment and the proximal abutment portion of the another intermediate segment abut each other when the articulated bending section body is bent at a maximum angle of the first bending plane, wherein when the articulated bending section body is bent at the maximum angle of the first bending plane a gap is formed between the outer rim of the one intermediate segment and the outer rim of the another intermediate segment, and wherein the sheath extends through the gap no further than the location where the distal abutment portion of the one intermediate segment and the proximal abutment portion of the another intermediate segment abut.

14. The system of claim 13, wherein the intermediate segments interconnected by the hinge members on the first bending plane comprise a passive section of the articulated bending section body, the articulated bending section body further comprising an active section, the intermediate segments of the active section being interconnected by hinge members on the first bending plane and on a second bending plane.

15. The system of claim 14, wherein the pull-wire passage in each intermediate segment in the active section extends through a hinge member of the hinge members on the second bending plane.

16. The system of claim 14, wherein the intermediate segments in the active section comprise pairs of intermediate segments, each pair connected to another pair by the hinge members on the first bending plane, and each intermediate segment of the pair connected to the other by the hinge members on the second bending plane.

17. An endoscope comprising:

an articulated bending section body including segments interconnected by hinge members on a first bending plane, the segments including a proximal segment, a distal segment and intermediate segments arranged between the proximal segment and the distal segment, a sheath positioned over the articulated bending section body; and a pull-wire, wherein each intermediate segment comprises a pull-wire passage, an outer rim, a distal surface and a proximal surface, the distal surface of one intermediate segment facing the proximal surface of another segment positioned adjacent to the one segment, the proximal surface and the distal surface each extending from the outer rim of the respective intermediate segment to a hinge member of the hinge members, the pull-wire extending through the pull-wire passages, wherein the one intermediate segment comprises a distal abutment portion and the another intermediate segment comprises a proximal abutment portion, wherein the pull-wire is configured to cause the distal abutment portion of the one intermediate segment and the proximal abutment portion of the another intermediate segment to abut each other at a location intermediate the outer rims and the hinge member to maintain apart the outer rim of the one intermediate segment from the outer rim of the another intermediate segment, a sheath pocket being formed between the outer rims, the distal abutment portion and the proximal abutment portion when the distal abutment portion and the proximal abutment portion abut each other, wherein each of the pull-wire passages comprises a radially outward peripheral portion and a radially inward peripheral portion radially opposite the radially outward peripheral portion, the radially outward peripheral portion limiting radially outward movement of the pull-wire, and wherein the radially outward peripheral portion of the pull-wire passage is radially inward of the sheath pocket to prevent contact between the pull-wire and the sheath, wherein the pull-wire passage of the one intermediate segment comprises an opening at the distal abutment portion and the pull-wire passage of the another intermediate segment comprises an opening at the proximal abutment portion.

18. The endoscope of claim 17, wherein the articulated bending section body further comprises a second bending plane orthogonal to the first bending plane, and wherein the opening of the pull-wire passage of the one intermediate segment and the opening of the pull-wire passage of the another intermediate segment are traversed by the second bending plane.

19. The endoscope of claim 1, wherein the articulated bending section body further comprises a second bending plane orthogonal to the first bending plane, and wherein the pull-wire configured to cause the distal abutment portion of the one intermediate segment and the proximal abutment portion of the another intermediate segment to abut each other extends through a hinge member of the hinge members traversed by the second bending plane.

20. The endoscope of claim 17, wherein the articulated bending section body comprises an active section and a passive section, wherein the passive section comprises segments of the segments interconnected by the hinge members on the first bending plane, wherein the active section comprises segments of the segments interconnected by the hinge members on the first bending plane and on a second bending plane, and wherein the active section is distal of the first bending section.

21. The endoscope of claim 20, wherein the pull-wire passages of the intermediate segments in the active section extend through hinge members of the hinge members on the second bending plane.

22. The endoscope of claim 20, wherein the intermediate segments in the active section comprise pairs of intermediate segments, each pair connected to another pair by the hinge members on the first bending plane, and each intermediate segment of the pair connected to the other by the hinge members on the second bending plane.

23. The endoscope of claim 20, wherein the pull-wire is enclosed in a sheath, wherein the sheath extends through the passive section and does not extend through the active section of the articulated bending section body, and wherein the pull-wire extends through the passive section and the active section of the articulated bending section body.

\* \* \* \* \*